US008246802B2

(12) United States Patent
Mezic et al.

(10) Patent No.: US 8,246,802 B2
(45) Date of Patent: Aug. 21, 2012

(54) SMALL VOLUME LIQUID MANIPULATION, METHOD, APPARATUS AND PROCESS

(75) Inventors: Igor Mezic, Goleta, CA (US); Frederic Bottausci, Santa Barbara, CA (US); Jason S. Spievak, Santa Barbara, CA (US); Peter J. Strand, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 971 days.

(21) Appl. No.: 12/120,620

(22) Filed: May 14, 2008

(65) Prior Publication Data

US 2009/0032398 A1 Feb. 5, 2009

Related U.S. Application Data

(60) Provisional application No. 60/917,796, filed on May 14, 2007.

(51) Int. Cl.
*B01D 57/02* (2006.01)
(52) U.S. Cl. ..................... 204/450; 204/600
(58) Field of Classification Search .......... 204/600, 204/450; 435/283.1, 287.2, 288.5, 288.6; 422/68.1, 100, 99, 72, 63, 64; 137/808, 827
See application file for complete search history.

(56) References Cited

U.S. PATENT DOCUMENTS 4,882,281 A * 11/1989 Hilliard et al. ............ 435/285.2
6,589,786 B1 * 7/2003 Mangano et al. ............ 435/372
8,034,226 B2 * 10/2011 Pham et al. .................. 204/643

FOREIGN PATENT DOCUMENTS

WO  WO2006/037910  * 4/2006

OTHER PUBLICATIONS

Arnold, W.M. et al., "Cell isolation and growth in electric-field defined micro-wells," Current Applied Physics, 2006, pp. 371-374, vol. 6.
Chang, D.E. et al., "Closed-form solutions in the electrical field analysis for dielectrophoretic and travelling wave inter-digitated electrode arrays," J. Phys. D: Appl. Phys., 2003, pp. 3073-3078, vol. 36.
Fixe, F. et al., "Electric-field assisted immobilization and hybridization of DNA oligomers on thin-film microchips," Nanotechnology, 2005, pp. 2061-2071, vol. 16.
Green, N.G. et al., "Fluid flow induced by nonuniform ac electric fields in electrolytes on microelectrodes. I. Experimental Measurements," Physical Review E, Apr. 2000, pp. 4011-4018, vol. 61, No. 4.

(Continued)

*Primary Examiner* — Alex Noguerola
*Assistant Examiner* — Gurpreet Kaur
(74) *Attorney, Agent, or Firm* — Venable LLP; Henry J. Daley

(57) ABSTRACT

An apparatus, a method and a process to achieve manipulation of particles and/or solutions through the use of electrokinetic properties are disclosed. The manipulation is performed using a disposable device positioned on top of a stage for purposes of powering the electrodes. The fluidic solution is brought into contact with the active part of the device and then manipulated.

5 Claims, 6 Drawing Sheets

OTHER PUBLICATIONS

Green, N.G. et al., "Fluid flow induced by nonuniform ac electric fields in electrolytes on microelectrodes. III. Observation of streamlines and numerical simulation," Physical Review E, 2002, pp. 026305-1-026305-11, vol. 66.

Hartmann, M. et al., "Increasing robustness and sensitivity of protein microarrays through microagitation and automation," Analytica Chimica Acta, 2006, pp. 66-73, vol. 564.

Liu, J. et al., "Enhanced Signals and Fast Nucleic Acid Hybridization by Microfluidic Chaotic Mixing**", Angew. Chem. Int. Ed., 2006, pp. 3618-3623, vol. 45.

Liu, R.H. et al., "Acoustic micromixer for enhancement of DNA biochip systems," J. Microlith., Microfab., Microsyst., Jul. 2003, pp. 178-184, vol. 2, No. 3.

Marshall, A. et al., "DNA chips: an array of possibilities," Nat. Biotechnol., 1998, pp. 27-31, vol. 16.

Morgan, H. et al., "Separation of Submicron Bioparticles by Dielectrophoresis," Biophysical Journal, Jul. 1999, pp. 516-525, vol. 77.

Muller, T. et al., "A 3-D microelectrode system for handling and caging single cells and particles," Biosensors & Bioelectronics, 1999, pp. 247-256, vol. 14.

Pethig, R. et al., "Positive and negative dielectrophoretic collection of colloidal particles using interdigitated castellated microelectrodes," J. Phys. D: Appl. Phys., 1992, pp. 881-888, vol. 24.

Ramos, A. et al., "Ac Electrokinetics: a review of forces in microelectrode structures," J. Phys. D: Appl. Phys., 1998, pp. 2338-2353, vol. 31.

Sasakura, Y. et al., "Microarray techniques for more rapid protein quantification: Use of single spot multiplex analysis and a vibration reaction unit," Analytica Chimica Acta, 2006, pp. 53-58, vol. 564.

Sigurdson, M. et al., "Electrothermal stirring for heterogeneous immunoassays," Lab on a Chip, 2005, pp. 1366-1373, vol. 5.

Southern, E. et al., "Molecular interactions on microarrays," Nat. Genet. Supplement, 1999, pp. 5-9, vol. 21.

Squires, T.M. et al., "Induced-charge electro-osmosis," J. Fluid Mech., 2004, pp. 217-252, vol. 509.

Suehiro, J. et al., "The dielectrophoretic movement and positioning of a biological cell using a three-dimensional grid electrode system," J. Phys. D: Appl. Phys., 1998, pp. 3298-3305, vol. 31.

Tuval, I. et al., "Control of particles in microelectrode devices," Physical Review Letters, Dec. 2005, pp. 236002-1-236002-4, vol. 95, No. 23.

Vanderhoeven, K. et al., "DNA Microarray Enhancement Using a Continuously and Discontinuously Rotating Microchamber," Anal. Chem., 2005, pp. 4474-4480, vol. 77.

Voldman, M. et al., "Design and analysis of extruded quadrupolar dielectrophoretic traps," Journal of Electrostatics, 2003, pp. 69-90, vol. 57.

Xiang, C.C. et al., "cDNA microarray technology and its applications," Biotechnol. Adv., 2000, pp. 35-46, vol. 18.

Yang, R-J. et al., "Electroosmotic Flow in Microchannels," Journal of Colloid and Interface Science, 2001, pp. 98-105, vol. 239.

Yuen, P.K. et al., "Microfluidic devices for fluidic circulation and mixing improve hybridization signal intensity on DNA arrays," Lab on a Chip, 2003, pp. 46-50, vol. 3.

* cited by examiner

SMALL VOLUME LIQUID MANIPULATION, METHOD, APPARATUS AND PROCESS

CROSS-REFERENCE TO RELATED APPLICATIONS

This application claims the benefit under 35 U.S.C. Section 119(e) of and commonly-assigned U.S. Provisional Patent Application Ser. No. 60/917,796 filed on May 14, 2007, by Igor Mezic et al., entitled "SMALL VOLUME LIQUID MANIPULATION, METHOD, APPARATUS, AND PROCESS," which application is incorporated by reference herein.

STATEMENT REGARDING FEDERALLY SPONSORED RESEARCH AND DEVELOPMENT

This invention was made with Government support under Grant No. DMS-0507256 awarded by the NSF. The Government has certain rights in this invention.

BACKGROUND OF THE INVENTION

1. Field of the Invention

The present invention relates in general to the field of manipulating fluid flow and/or particle motivating force and is related to separation, concentration, transport, reaction and mixing apparatus, method and process. More particularly, the present invention relates to improved manipulation by bringing the present invention in contact with the solution. Moreover, the invention can be embedded into existing liquid-containing vessels such as well-plates and microarrays.

2. Description of the Related Art (Note: This application references a number of different publications as indicated throughout the specification by one or more reference numbers within brackets, e.g., [x]. A list of these different publications ordered according to these reference numbers can be found below in the section entitled "References." Each of these publications is incorporated by reference herein.)

Devices using electrokinetic properties (electrophoresis, dielectrophoresis, electroosmosis and electrothermal convection) have been used to manipulate fluids and particles.

Electrophoresis is a technique for manipulating components of a mixture of charged molecules (proteins, DNAs, or RNAs) in an electric field within a gel or other support. Under AC electric field, uncharged particles suspended in a dielectric media can be polarized and further manipulated. If the field is spatially inhomogeneous, it exerts a net force on the polarized particle known as dielectrophoretic (DEP) force [1]. This force depends upon the temporal frequency and spatial configuration of the field as well as on the dielectric properties of both the medium and the particles. Single frequency electric fields can be used to transport and separate particles.

Fluid motion can also be induced by applying an electric field onto a solution. The force driving the fluid thus originates in the bulk (buoyancy, electrothermal effect) or at the interface between the fluid and the device containing the fluid (electroosmosis).

The buoyancy generates a flow because of a density gradient. It can be produced by internal or external heating. An electric field is often used as internal energy source. Applied to a solution, part of the electric energy dissipates in the fluid by Joule effect and locally heats the fluid. Furthermore, local heating creates gradients of conductivity and permittivity. The fluid can then move under the influence of an electrothermal flow [2, 3, 4].

Under certain conditions (material properties, conductivity and permeability of the fluid and the device containing the fluid), ion layers develop at the fluid-surface interface due to chemical associations or dissociations and physical adsorption on or desorption from the solid surface. Ion layers can also be generated at the surface of electrodes where a potential is externally imposed. Applying an electric field with a tangential component to the layers moves the ions which carry the fluid along by viscous force. This process produces a bulk flow [2, 3, 4].

Coupled with an electrohydrodynamic flow, several electrode geometries have been designed as a tool to manipulate fluids and particles. Interdigitated castellated electrodes are, for instance, designed to trap and separate particles [5, 6]. Polynomial electrodes [7], planar electrodes [8, 9], quadripolar electrodes [27] or more complex geometries [10] have also been proposed.

Micro Technology Applied to Biological Problems

Massively parallel hybridization [11-13] improves the way many biological and medical analyses are performed both in research and clinical applications, but there is still a lack of an efficient multipurpose device. As sample volumes used in massive parallel systems become smaller and smaller (micro- to nanoliter or even smaller) it is more challenging to manipulate the fluids since the fluid viscosity dominates any convection. Multiple reports have shown that micromixing, transport or concentration improves hybridization reaction [14-16,17, 18]. Micromixing can be achieved by ultrasonic agitation (the nucleation of bubbles creates small jets that enhance the mixing) [19] or by vortexing or agitating the solution and creating convection [20]. Micromixing can also be produced by surface wave generation [21] for instance.

What is needed then are improved methods, processes and general apparatus to efficiently and accurately mix, separate, concentrate, and transport small volume of fluids with or without particles (e.g., atoms, molecules, cells in biological and chemical assays) using combined fluid flow and/or electrokinetic methods. The present invention satisfies that need.

SUMMARY OF THE INVENTION

The present invention discloses an apparatus, a method and a process to achieve manipulation of particles and/or solutions in a container. The invention uses electrokinetic properties. The manipulation is performed by bringing the fluidic solution into contact with the active part of the device. For the purpose of this document, a "vessel" will denote specifically either a microtiter plate (microplate or well-plate) well or more generally any volume containing liquid solution. The invention includes a process where one or more vessels with built in electrodes (made of any applicable material) are filled with one or more fluids or one or more fluids and one or more types of particles for the purpose of manipulating fluid(s) and/or particles. The manipulations can include concentration, separation, transport or mixing.

A device composed of two parts comprising vessels containing electrodes capable of inducing electrokinetic (including electroosmotic and electrothermal) fluid flow inside vessels (including microplates or well-plates) and a connecting plate (the vessels bloc being a separate entity from the connecting plate). The electrodes contacts or pads are accessible from outside the vessels. The electrodes are energized through the connecting plate by bringing into contact the electrodes contacts or pads with the connecting plate. The electrodes are built into the vessel, itself. The device can be used for general manipulation of fluids and particles inside the vessel, including concentration, separation, transport or mixing. The device is tunable, so that by applying different DC and/or AC voltages, different flow effects can be induced and adapted to efficiently manipulate the fluids and particles contained inside the vessel. The device can perform one or more particle manipulation operations.

A method where more than one frequency of AC field is used to induce fluid flows sequentially in time or simultaneously to induce fluid flow and electromagnetic field for the purpose of manipulating particles (including concentration, separation, transport or mixing of the particles). The flow and electromagnetic field can be applied by electrodes built into the device (thus being an integral part of the device) or applied externally. A device for manipulating fluidic solutions in accordance with the present invention comprises a vessel for containing a fluidic solution, and a plurality of electrodes, coupled to the vessel, the plurality of electrodes being arranged in an array and each applying an electric field to the fluidic solution, wherein the plurality of electrodes manipulate at least one of a flow of the fluidic solution and a separation of particles in the fluidic solution, the manipulation using electrokinetic properties resulting from the applied electric fields, wherein the fluidic solution comprises a total volume of fluid on the order of microliters.

Such a device further optionally comprises the electrokinetic property is at least one of electrothermal convection and electroosmosis, at least a first electrode in the plurality of electrodes being made from a first material and at least a second electrode in the plurality of electrodes being made from a second material, the array being a periodic array, each electrode in the periodic array being controlled independently, at least a first electrode in the plurality of electrodes having a first shape and at least a second electrode in the plurality of electrodes having a second shape, and the electric field inducing a time-dependent electrohydrodynamic fluid flow.

A method in accordance with the present invention comprises forming at least one recurrent circulating fluid flow within the fluid, introducing at least one particle motivating force to the fluid having the recurrent circulating fluid flow, and manipulating the at least one particle motivating force using electrokinetic properties, the particle motivating force comprising at least applied electric fields, wherein the fluidic solution comprises a total volume of fluid on the order of microliters.

Such a method further optionally comprises at least one particle motivating force directionally interacting with the at least one recurrent circulating fluid flow in a tangential orientation relative to the recurrent circulating fluid flow, the at least one particle motivating force directionally interacting in a tangential orientation at a periphery of the at least one recurrent circulating fluid flow, collecting the particles, and applying a time-dependent electrohydrodynamic fluid flow.

Another device in accordance with the present invention comprises a vessel for containing the fluid to be mixed, a plurality of electrodes, inside the vessel, and a plurality of connectors, coupled to the plurality of electrodes, the plurality of connectors being electrically coupled to a plurality of applied electric fields, wherein the plurality of electric fields electrically excite the electrodes thereby creating a flow within the fluid.

Such a device further optionally comprises the plurality of electric fields generating at least one of electrothermal convection and electroosmosis within the fluid, at least a first electrode in the plurality of electrodes being made from a first material and at least a second electrode in the plurality of electrodes being made from a second material, the plurality of electrodes being arranged in a periodic array, each electrode in the periodic array being controlled independently, at least a first electrode in the plurality of electrodes having a first shape and at least a second electrode in the plurality of electrodes having a second shape, and the electric field inducing a time-dependent electrohydrodynamic fluid flow.

BRIEF DESCRIPTION OF THE DRAWINGS

Referring now to the drawings in which like reference numbers represent corresponding parts throughout:

FIG. 2(a) shows the vessels on top of the holding plate with the electrodes connectors on the backside on the plate. FIG. 2(b) shows the vessels inserted into the holding plate with the electrodes connectors on the bottom of the vessels. FIG. 2(c) shows the electrodes directly inserted into the holding plate with the electrodes connectors on the backside of the plate.

FIG. 6(a) is a drawing of aligned cylindrical electrodes, FIG. 6(b) is a drawing of cylindrical electrodes arranged in staggered row, FIG. 6(c) is a drawing of cylindrical electrodes with different length arranged in staggered row, FIG. 6(d) is a drawing of cylindrical and circular electrodes, and FIG. 6(e) is a drawing of curved cylindrical electrodes. The electrodes can also be mounted on the plate without a container around them.

DETAILED DESCRIPTION OF THE INVENTION

Figure 1:
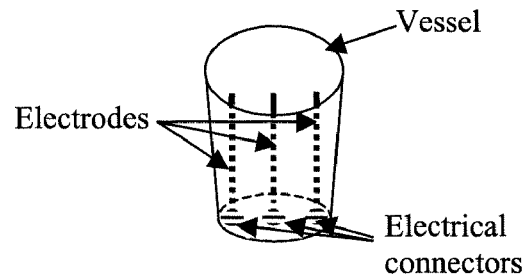
FIG. 1 illustrates an example of the arrangement of the electrode arrays inside a vessel. The electrodes connectors are on the bottom of the vessel.

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Overview

The impact of the manipulation of fluids and/or particles induced by electric fields is described theoretically and experimentally herein. By means of a microfluidic device comprising a periodic array of microelectrodes, fluid(s) and/or particles manipulations are shown including concentration, separation, transport or mixing using electrokinetic properties. The theoretically predicted dynamical phenomena are demonstrated experimentally.

This invention could be used, for example, to improve the mixing of microliter or nanoliter volume protein solutions analyzed in high throughput screening assays. Electrokinetic micromixing improves the time and reliability for protein expression by rapidly homogenizing the small volume solution. Current methods require extensive human or robotic operations and generally lack the required sensitivity to meet reliability testing standards. Other possible applications could be the separation and detection of small populations of pre-cancerous cells from body fluids (blood, sputum, urine) or the concentration of DNA particles inside a Polymerase Chain Reaction (PCR) apparatus for improved DNA detection.

Technical Description

The present invention discloses an apparatus, a method and a process to achieve manipulation of particles and/or solution in micro- to nanoliter volumes. Volumes on the order of microliters means that the total volume of the fluid is less than one milliliter, but the device can be used with total volumes greater than one milliliter if desired. The device of this invention uses electrokinetic properties. The manipulation is performed by positioning vessels onto the electrodes arrays for purpose of powering the electrodes, bringing the fluidic solution considered into contact with the active part of the device in the vessels and applying precise and carefully chosen electric fields combinations. The purpose of the active part of the device is to manipulate the flow and/or particles using an electric field.

Electric fields induce a force on charged particles in solutions, moving the particles towards either the cathode or the anode depending on the sign of the charged particles [22]. Such a particle motion in liquid phase is called electrophoresis. If the particle is uncharged, applying AC-electric field to the medium containing the particles creates a dipole on the particles. The orientation of the dipole depends on the conductivity and permittivity of both the particles and the medium. For dielectric particles, the expression of the time average force is given by $$\langle F_{DEP} \rangle = 2\pi a^3 \in_m Re[K(\omega)] \nabla |E|^2$$

where E is the rms electric field, a is the particle radius, $\omega$ is the angular field frequency, and Re[z] indicates the real part of the complex number z. The factor $K(\omega)$ is a measure of the effective polarizability of the particle, known as the Clausius-Mossotti factor, given by $$K(\omega) = (\in_p^* - \in_m^*)/(\in_p^* + 2\in_m^*)$$

where $\in_p^*$ and $\in_m^*$ are the complex permittivities of the particle and the medium, respectively. The complex permittivity is defined as $\in^* = \in - i(\sigma/\omega)$, where $i = \sqrt{-1}$, $\in$ is the permittivity, and $\sigma$ is the conductivity.

The particles submitted to a non uniform electric field will move toward or away from the high electric field region depending on the sign of $Re[K(\omega)]$. The motion of the particles is called dielectrophoresis.

Electrophoresis and dielectrophoresis are two major subjects in particle separation and transport. For separation purposes, let's consider a common case where two types of particles are present in the solution.

Separation occurs when there is a frequency $\omega_s$ for which $Re[K(\omega)]$ takes a different sign for each particle type. For particles having close properties $\omega_s$ might be impossible to apply experimentally. In that case [23] have shown that two superposed AC-electric fields with two different frequencies $\omega_{s1}$ and $\omega_{s2}$ enables the particle separation. $\omega_{s1}$ and $\omega_{s2}$ being two frequencies for which each particle type has a Clausius-Mossotti factor of opposite sign.

Consider a simple but commonly used configuration of an electrode array for which a closed-form solution of the electric field and the DEP force was derived in [23]. It is comprised of a periodic array of long parallel micro-electrodes. Each electrode submitted to an AC-electric field with a defined phase difference with their neighbors will simultaneously separate and transport the particles through the system [23]. The process is named traveling wave dielectrophoresis.

Electric fields induce fluid and/or particle motions through several electro-hydrodynamic, electrophoretic or dielectrophoretic effects. Among all the effects the flow is submitted to, the most important in microelectrode devices are electrothermal convection and electroosmosis. The former appears to be due to a non-uniform Joule heating of the fluid which leads to gradients of its permittivity and conductivity. The applied electric fields acting on the permittivity and conductivity gradients generate electrical body forces that induce the flow [13]. The latter is caused by electrical stresses in the diffuse double layer of charges accumulated above the electrodes (AC-electroosmosis) [14] or at the walls (electroosmosis) [24]. These stresses result in a rapidly varying fluid velocity profile in the diffuse double layer, going from zero at the wall to a finite value just outside the double layer. Whether electrothermal or AC-electroosmotic flows dominate the motion of fluid in the device depends mainly on the frequency of the applied electric field and the conductivity of the medium, AC-electroosmosis being dominant at a frequency range several orders of magnitude below the charge relaxation frequency ($\omega_c \approx \sigma/\in$) for low conductivity media.

If the applied frequency is chosen carefully, the induced effects will most affect the fluid flow and produce efficient mixing, for instance. Using multifrequency electric field signals [8] will, most of the time, improve even more the flow manipulation.

Dielectrophoresis and fluid flow precisely combined make possible the manipulation of submicron particles. For a careful choice of the applied frequency, the electro-hydrodynamically induced fluid flows will have a minimal effect but will be determinant in the DEP manipulation and/or separation of submicron particles. It has been shown that the induced dynamical properties can be creatively used as a mechanism to control micro or submicron particles. Experiments and numerical simulations of the coupled electro-thermo-hydrodynamic problem in devices with interdigitated arrays of electrodes [12, 13, 14] or electrode poles [26] show that both electrothermal and AC-electroosmotic flows consist of convective rolls centered at the electrode edges and provide good estimates for their strength and frequency dependence. Near the electrodes, the fluid velocity $u_0$ ranges from 1 to 1000 $\mu m.s^{-1}$ decaying exponentially with the transversal distance to the electrodes.

Figure 7:
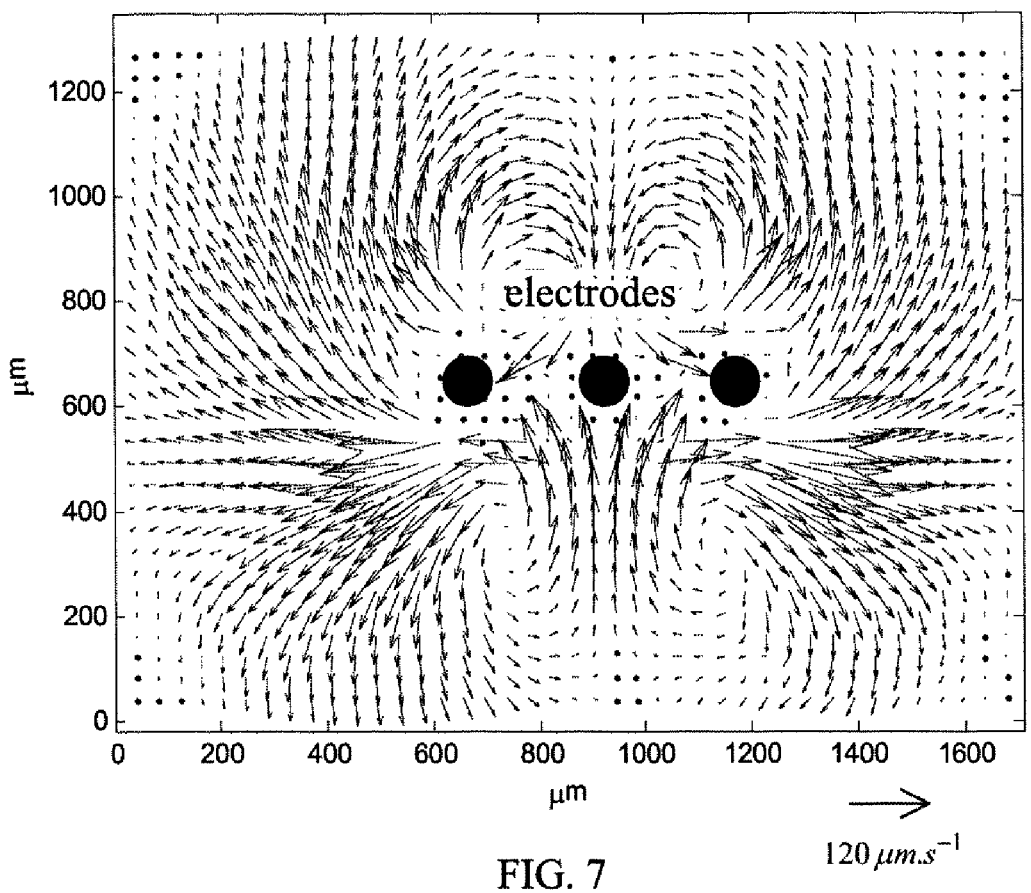
FIG. 7 is a graph that shows the velocity field in the plane orthogonal to the electrodes for the electrode configuration shown in FIG. 6(a). The velocity field is measured par Particle Image Velocimetry at mid height of a cell measuring 570 µm high, 2 mm wide and 2 mm long. The fluidic solution was water with conductivity $\sigma=0.6$ S.m$^{-1}$ seeded with 0.71 µm fluorescent particles. The signal applied was 530V.cm$^{-1}$ at 700 KHz.

In a device of characteristic length d=150 μm, fluid viscosity $v=10^{-6}$ m$^2$ s$^{-1}$, conductivity σ=0.6 S.m$^{-1}$ with AC-electric field of 530V/cm, the maximum flow velocity is measured to be 150 μm.s$^{-1}$ [FIG. 7].

The electric field induced heating inside the solution induces buoyancy flow effects. These are caused by gravity acting on nonhomogeneities in densities inside the liquid solution to induce flow. These are possibly used in the device in conjunction with electrokinetic/electrothermal effects to provide mixing, concentration, separation and transport effects.

Figure 6:
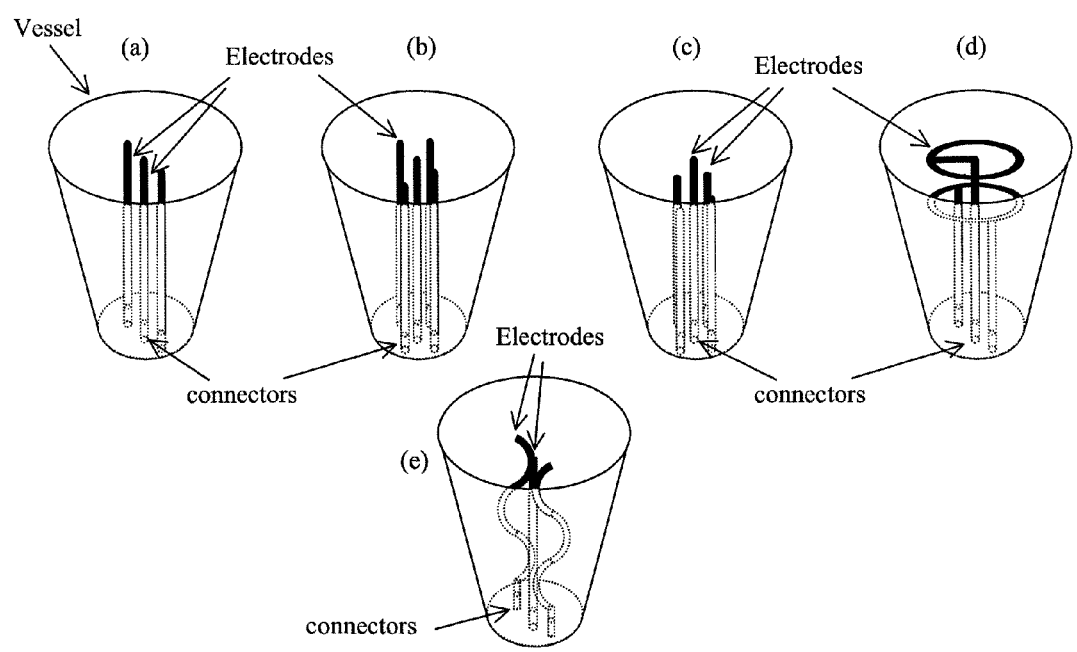
FIG. 6 is a block diagram that illustrates examples of the arrangement of the electrode inside a vessel.

The invention apparatus contains electrodes capable of producing any of the physical properties described in the sections above. The device is capable of inducing electrokinetic (including electroosmotic and electrothermal) fluid flow inside vessels (including microplates or well-plates and microarray hybridization solutions). The electrode arrays are designed to fit microliter size (or smaller) vessels as well as microliter (or smaller) droplets. The electrodes are generally micron sized wires shaped like [FIG. 6-FIG. 7]. For micromixing, one might prefer pole electrodes since the fluid can flow between the electrodes, for instance [FIG. 7]. The electrode array pitch is optimized depending on the application and the electric field strength.

Figure 2:
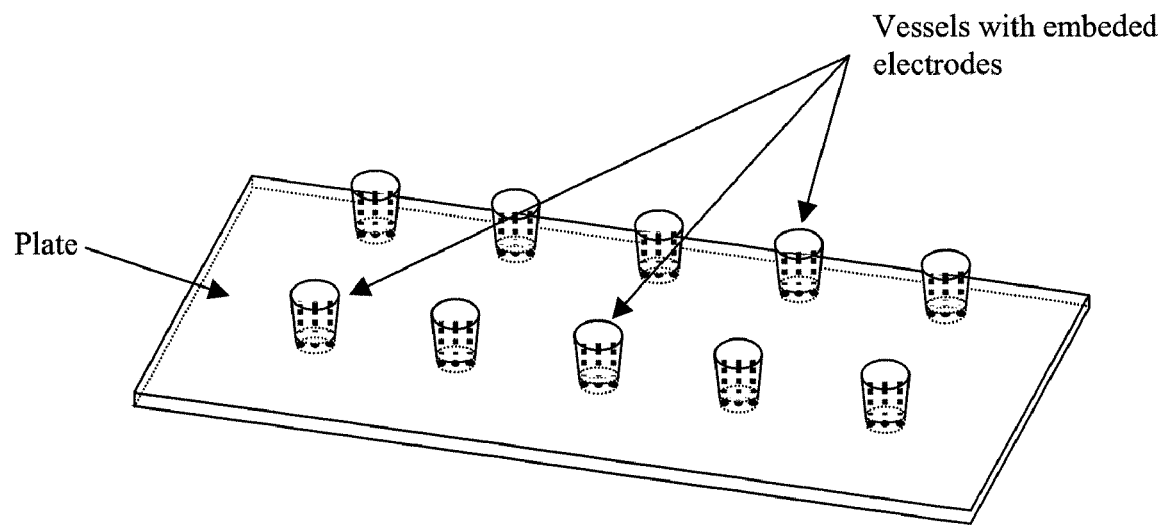
FIGS. 2(a) through 2(c) illustrate examples of the vessels (with embedded electrodes) arrangement to form a wells plate.
Figure 2:
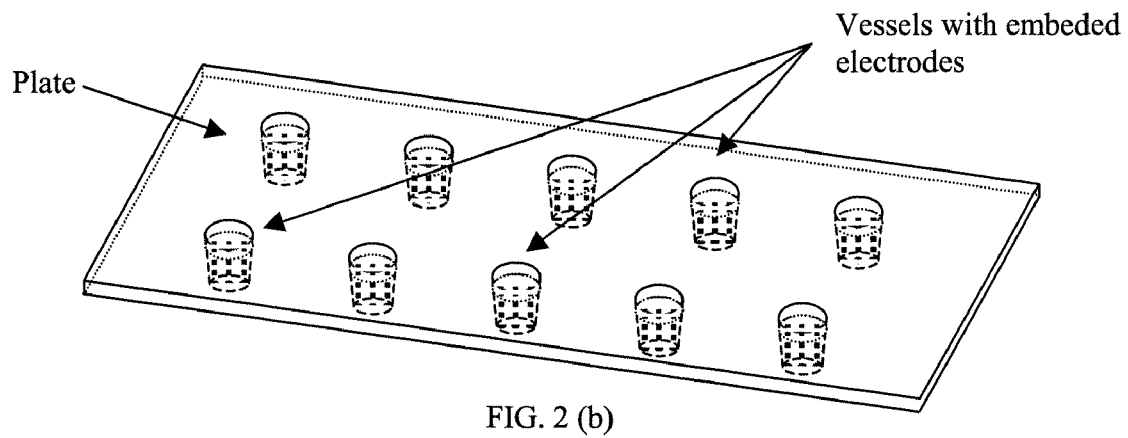
Figure 2:
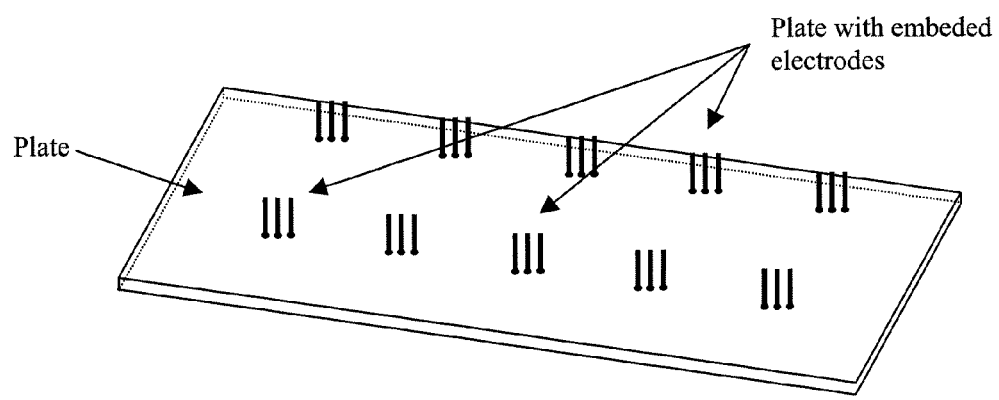
Figure 3:
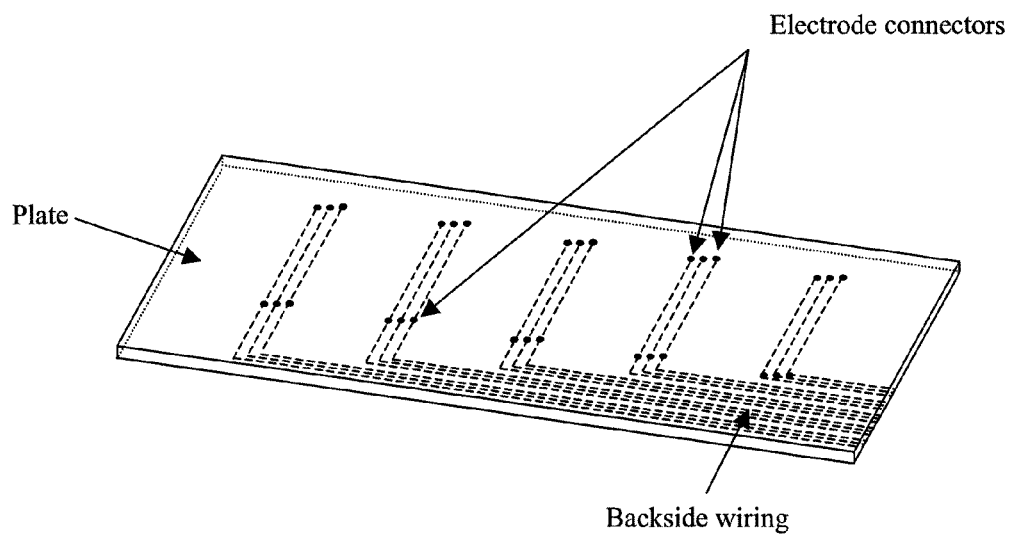
FIG. 3 illustrates an example of a connecting plate. In this example, each row can be controlled separately. The electrode pads (shown in detail in FIG. 4) are wired to link the electrode pads to an external controller. The wires are drawn on the backside of the plate in this example but can by on any side of the plate.
Figure 4:
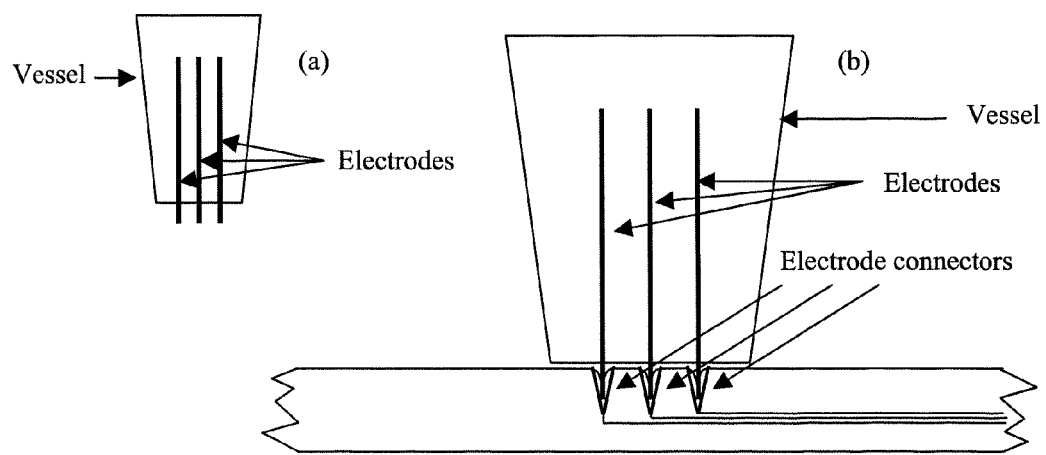
FIGS. 4(a) and 4(b) illustrates an example of a vessel with electrodes from a side view (a) and a connection on the electrodes array (b). The connectors of the array have conic shape with flexible conductive flaps designed to enable reliable contacts.
Figure 5:
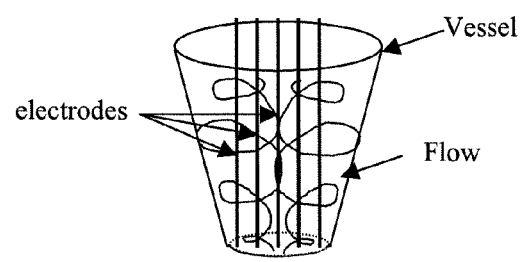
FIG. 5 is a drawing of a vessel with embedded electrodes with a streamline of the flow once the electrodes are energized.

For parallel applications like well-plates or microarrays, the device can comprise sets of individually tunable or not tunable electrode arrays as shown [FIG. 2].

The fluidic solution is either put in the vessels then the vessels, vessels array or vessels plate is inserted in the connecting plate or the vessels, vessels array or vessels plate is first inserted in the connecting plate then the vessels are filled. The vessels, vessels array or vessels plate can be disposable. The device can be used for general manipulation of fluids and particles inside the vessel, including concentration, separation, transport or mixing. The device is tunable, so that by applying different DC and/or AC voltages, different flow effects can be induced and adapted to efficiently manipulate fluids and particles contained inside the vessel. The device can perform one or more particle manipulation operations. The device is flexible. It can be tuned and adapted to a variety of configurations depending on the application.

The process of this invention is to bring the fluid and/or particle solution in contact with the electrodes and to bring the electrodes in contact with the connecting plate. The electrodes can be embedded within the vessel or plate. Bringing the solution in contact with the electrodes and applying the appropriate electric field will enable manipulation of the fluidic solution.

REFERENCES

Figure 8:
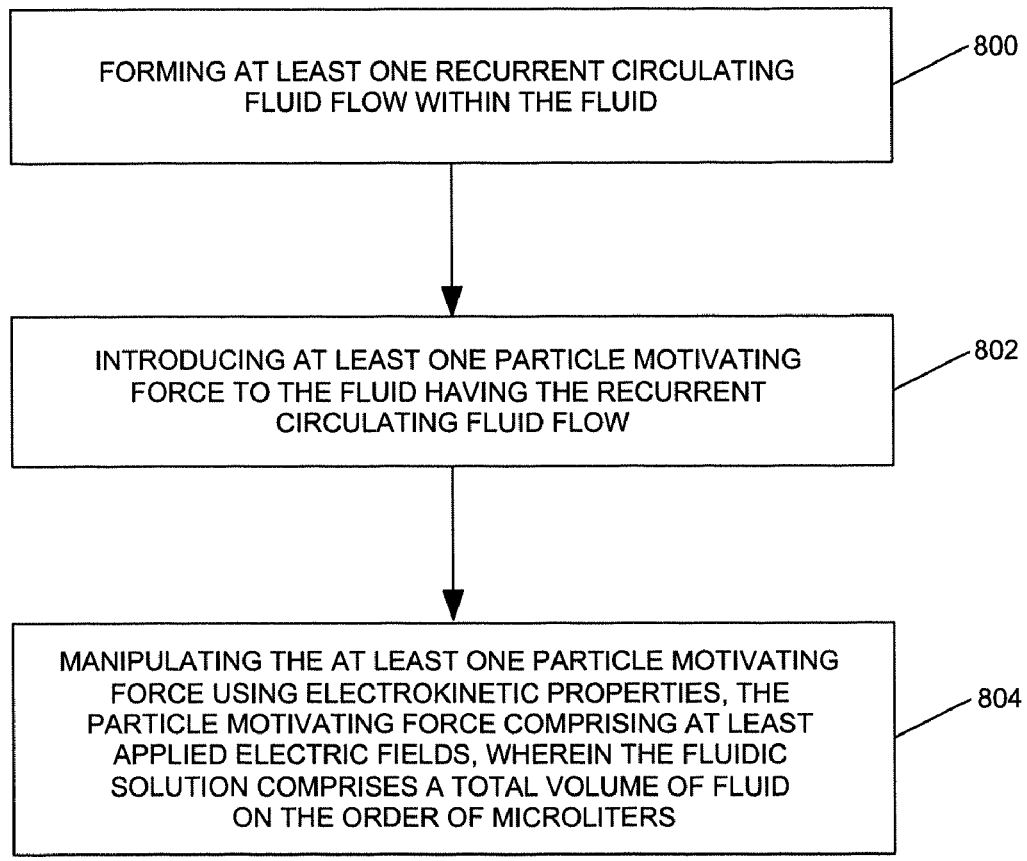
FIG. 8 is a process chart in accordance with the present invention.

The following references are incorporated by reference herein:
1. H. A. Pohl, Dielectrophoresis (Cambridge University Press, 1978).
2. N. G. Green, A. Ramos, A. Gonzalez, H. Morgan, A. Castellanos, Phys. Rev. E 61, 4011 (2000).
3. A. Ramos, H. Morgan, N. G. Green, A. Castellanos, J. Phys. D: Appl. Phys. 31, 2338 (1998).
4. N. G. Green, A. Ramos, A. Gonzalez, H. Morgan, A. Castellanos, Phys. Rev. E 66, 026305 (2002).
5. PETHIG R, HUANG Y, WANG X B, BURT J P H, "POSITIVE AND NEGATIVE DIELECTROPHORETIC COLLECTION OF COLLOIDAL PARTICLES USING INTERDIGITATED CASTELLATED MICROELECTRODES," Journal of Physics D-Applied Physics 25 (5): 881-888 May 14, 1992.
6. Arnold W M, Franich N R, Cell isolation and growth in electric-field defined micro-wells, APPLIED PHYSICS 6 (3): 371-374 JUN 2006
7. H. Morgan, M. P. Hughes, and N. G. Green, "Separation of submicron bioparticles by dielectrophoresis," *Biophysical Journal* 77 (1999) 516-525.
8. I. Tuval, I. Mezic, F. Bottausci, Y. T. Zhang, N. C MacDonald and O. Piro, *Control of particles in microelectrode devices*, Physical Review Letters 95(23) Dec. 2005
9. J. Suchiro, and R. Pethig, "The dielectrophoretic movement and positioning of a biological cell using a three-dimensional grid electrode system," *Journal of Physics D: Applied Physics* 31(1998) 3298-3305.
10. T. Müller, G. Gradl, S. Howitz, S. Shirley, T. Schnell, and G. Fuhr, A 3-D microelectrode system for handling and caging single cells and particles, *Biosensors & Bioelectronics* 14 (1999) 247-256.
11. Marshall A and Hodgson J 1998 DNA chips: an array of possibilities *Nat. Biotechnol.* 16 27.
12. Southern E, Mir K and Shchepinov M 1999 Molecular interactions on microarrays *Nat. Genet.* 21 (Suppl.) 5-9.
13. Xiang C C and Chen Y 2000 *Biotechnol. Adv.* 18 35-46.
14. Liu J, Williams B A, Gwirtz R M, Wold B J, Quake S, ANGEWANDTE CHEMIE-INTERNATIONAL EDITION 45 (22): 3618-3623 2006.
15. Yuen P K, Li G S, Bao Y J, Muller U R, Microfluidic devices for fluidic circulation and mixing improve hybridization signal intensity on DNA arrays LAB ON A CHIP 3 (1): 46-50 2003.
16. Sasakura Y, Kanda K, Fukuzono S, Microarray techniques for more rapid protein quantification: Use of single spot multiplex analysis and a vibration reaction unit, ANALYTICA CHIMICA ACTA 564 (1): 53-58 Mar. 30, 2006.
17. F Fixe, H M Branz, N Louro, V Chul, D M F Prazeres and J P Conde, Electric-field assisted immobilization and hybridization of DNA oligomers on thin-film microchips, Nanotechnology 16 (2005) 2061-2071.
18. Sigurdson M, Wang D Z, Meinhart C D, Electrothermal stirring for heterogeneous immunoassays, LAB ON A CHIP 5 (12): 1366-1373 2005.
19. Robin H. Liu, Ralf Lenigk, Piotr Grodzinski, Acoustic micromixer for enhancement of DNA biochip systems J.Microlith., Microfab., Microsyst., Vol. 2 No. 3, Jul. 2003 179.
20. J Vanderhoeven, K, Pappaert, B, Dutta, P. V, Hummelen and G. Desmet DNA Microarray Enhancement Using a Continuously and Discontinuously Rotating Microchamber, Anal. Chem. 2005, 77, 4474-4480.
21. M. Hartmann a, A. Toeglb, R. Kirchner b, M. F. Templin a, T. O. Joos, Increasing robustness and sensitivity of protein microarrays through microagitation and automation *Analytica Chimica Acta* 564 (2006) 66-73.
22. D. Li, electrokinetics in microfluidics, Elsevier Academic Boston 2004.
23. D. E. Chang, S. Loire, I. Mezic, J. Phys. D: Appl. Phys. 36, 3073 (2003).
24. Yang R J, Fu L M, Lin Y C, Electroosmotic flow in microchannels, JOURNAL OF COLLOID AND INTERFACE SCIENCE 239 (1): 98-105 Jul. 1, 2001.
26. Squires T M, Bazant M Z, Induced-charge electro-osmosis, JOURNAL OF FLUID MECHANICS 509: 217-252 Jun. 25, 2004
27. J. Voldman, M. Toner, M. L. Gray, and M. A. Schmidt, Design and analysis of extruded quadrupolar dielectrophoretic traps, *Journal of Electrostatics* 57 (2003) 69-90
Process Chart FIG. 8 illustrates a process chart in accordance with the present invention.

Box 800 illustrates forming at least one recurrent circulating fluid flow within the fluid.

Box 802 illustrates introducing at least one particle motivating force to the fluid having the recurrent circulating fluid flow.

Box 804 illustrates manipulating the at least one particle motivating force using electrokinetic properties, the particle motivating force comprising at least applied electric fields, wherein the fluidic solution comprises a total volume of fluid on the order of microliters.

CONCLUSION

In this invention, we claim a device composed of two parts. One part containing electrodes used to manipulate solutions. The electrodes can be embedded on vessels or on a plate. This part can be disposable. The other part is used to connect the electrodes of the vessels. This second part is used to interface an external controller (which sends signals to the electrodes embedded in the vessels) to the electrodes in order to manipulate the said fluids or complex solutions. Part of the device has built in electrodes that can be used to manipulate fluids or solutions by creating electric fields. Once an electric field is applied, electrokinetic effects are generated.

In this invention, we claim a method to manipulate fluids or fluidic solutions by creating electric fields with electrodes in direct or indirect contact with fluids or fluidic solutions.

In this invention, we claim a process to manipulate fluids or fluidic solutions by creating electric fields with electrodes in direct or indirect contact with fluids or fluidic solutions. The process implies to bring one or more fluids or fluidic solutions in contact with electrodes. The electrodes are energized, and a force is transmitted to the fluids.

A device for manipulating fluidic solutions in accordance with the present invention comprises a vessel for containing a fluidic solution, and a plurality of electrodes, coupled to the vessel, the plurality of electrodes being arranged in an array and each applying an electric field to the fluidic solution, wherein the plurality of electrodes manipulate at least one of a flow of the fluidic solution and a separation of particles in the fluidic solution, the manipulation using electrokinetic properties resulting from the applied electric fields, wherein the fluidic solution comprises a total volume of fluid on the order of microliters.

Such a device further optionally comprises the electrokinetic property is at least one of electrothermal convection and electroosmosis, at least a first electrode in the plurality of electrodes being made from a first material and at least a second electrode in the plurality of electrodes being made from a second material, the array being a periodic array, each electrode in the periodic array being controlled independently, at least a first electrode in the plurality of electrodes having a first shape and at least a second electrode in the plurality of electrodes having a second shape, and the electric field inducing a time-dependent electrohydrodynamic fluid flow.

A method in accordance with the present invention comprises forming at least one recurrent circulating fluid flow within the fluid, introducing at least one particle motivating force to the fluid having the recurrent circulating fluid flow, and manipulating the at least one particle motivating force using electrokinetic properties, the particle motivating force comprising at least applied electric fields, wherein the fluidic solution comprises a total volume of fluid on the order of microliters.

Such a method further optionally comprises at least one particle motivating force directionally interacting with the at least one recurrent circulating fluid flow in a tangential orientation relative to the recurrent circulating fluid flow, the at least one particle motivating force directionally interacting in a tangential orientation at a periphery of the at least one recurrent circulating fluid flow, collecting the particles, and applying a time-dependent electrohydrodynamic fluid flow.

Another device in accordance with the present invention comprises a vessel for containing the fluid to be mixed, a plurality of electrodes, inside the vessel, and a plurality of connectors, coupled to the plurality of electrodes, the plurality of connectors being electrically coupled to a plurality of applied electric fields, wherein the plurality of electric fields electrically excite the electrodes thereby creating a flow within the fluid.

Such a device further optionally comprises the plurality of electric fields generating at least one of electrothermal convection and electroosmosis within the fluid, at least a first electrode in the plurality of electrodes being made from a first material and at least a second electrode in the plurality of electrodes being made from a second material, the plurality of electrodes being arranged in a periodic array, each electrode in the periodic array being controlled independently, at least a first electrode in the plurality of electrodes having a first shape and at least a second electrode in the plurality of electrodes having a second shape, and the electric field inducing a time-dependent electrohydrodynamic fluid flow.

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto and the full range of equivalents of the claims appended hereto.

What is claimed is:

1. A method for dynamically separating and concentrating particles in a fluid, said method comprising:
   forming at least one recurrent circulating fluid flow within the fluid, wherein the fluid is contained in at least one vessel of a plurality of vessels; and
   introducing at least one particle motivating force to the fluid having the recurrent circulating fluid flow; and
   manipulating the at least one particle motivating force using electrokinetic properties by selectively addressing at least two electrodes out of a plurality of electrodes, the particle motivating force comprising at least applied electric fields, wherein the fluidic solution comprises a total volume of fluid on the order of microliters.

2. The method of claim 1, wherein the at least one particle motivating force directionally interacts with the at least one recurrent circulating fluid flow in a tangential orientation relative to the recurrent circulating fluid flow.

3. The method of claim 2, wherein the at least one particle motivating force directionally interacts in a tangential orientation at a periphery of the at least one recurrent circulating fluid flow.

4. The method of claim 2, further comprising collecting the particles.

5. The method of claim 2, further comprising applying a time-dependent electrohydrodynamic fluid flow.

\* \* \* \* \*